United States Patent
Olson et al.

[11] Patent Number: 5,888,728
[45] Date of Patent: Mar. 30, 1999

[54] HAPTEN DERIVATIZED CAPTURE MEMBRANE AND DIAGNOSTIC ASSAYS USING SUCH MEMBRANE

[75] Inventors: John D. Olson, Sunnyvale; Robert F. Zuk, Burlingame; Richard D. Armenta, Sunnyvale; Charles R. Burke, Palo Alto; Viola T. Kung; Edward L. Sheldon, both of Menlo Park, all of Calif.

[73] Assignee: Molecular Devices Corporation, Sunnyvale, Calif.

[21] Appl. No.: 484,968

[22] Filed: Jun. 7, 1995

Related U.S. Application Data

[63] Continuation of Ser. No. 364,522, Dec. 27, 1994, abandoned, which is a continuation of Ser. No. 490,644, May 24, 1990, abandoned, which is a continuation-in-part of Ser. No. 258,894, Oct. 17, 1988, abandoned.

[51] Int. Cl.[6] .......................... C12Q 1/68; G01N 33/566; C07H 19/00; C07H 21/00
[52] U.S. Cl. ................ 435/6; 435/442; 436/501; 436/530; 436/532; 436/543; 436/63; 436/823; 536/22.1; 536/25.32
[58] Field of Search ................... 435/6, 172.3; 436/501, 436/530, 532, 543, 63, 823; 935/77, 78, 110; 536/22.1, 25.32

[56] References Cited

U.S. PATENT DOCUMENTS

| | | | |
|---|---|---|---|
| 4,410,634 | 10/1983 | Cooper et al. | 436/500 |
| 4,478,914 | 10/1984 | Giese | 428/407 |
| 4,496,654 | 1/1985 | Katz et al. | 435/7 |
| 4,820,644 | 4/1989 | Shäfer et al. | 436/518 |
| 4,978,608 | 12/1990 | Kung et al. | 435/6 |

FOREIGN PATENT DOCUMENTS

| | | |
|---|---|---|
| 0 122 209 | 10/1984 | European Pat. Off. . |
| 0 269 092 | 6/1988 | European Pat. Off. . |
| WO 85/03356 | 8/1995 | WIPO . |

OTHER PUBLICATIONS

Wilchek et al., "Review. The avidin–biotin complex in bioanalytical applications" Analytical Biochemistrry, vol. 171, pp. 1–32 1988.

Syvanen et al. "Fast quantification of nucleic acid hybrids by affinity–based hybrid collection" Nucleic Acids Research, vol. 14 No. 12, pp. 5037–5048, 1986.

Chelly et al. "Transcription of the dystrophin gene in human muscle and non–muscle tissues". Nature, vol. 333, pp. 858–860, 1988.

*Primary Examiner*—Ardin H. Marschel
*Assistant Examiner*—Jezia Riley
*Attorney, Agent, or Firm*—McDonnell, Boehnen Hulbert & Berghoff

[57] ABSTRACT

The present invention encompasses a capture membrane comprising a porous filter membrane having a hapten bound directly or indirectly to the membrane wherein complexes formed by specific binding having an anti-hapten bound to a binding member of the specifically binding complex are removed from a solution by the hapten as the solution passes through the membrane. In the preferred embodiment biotin is the hapten and avidin or streptavidin is the anti-hapten.

27 Claims, 4 Drawing Sheets

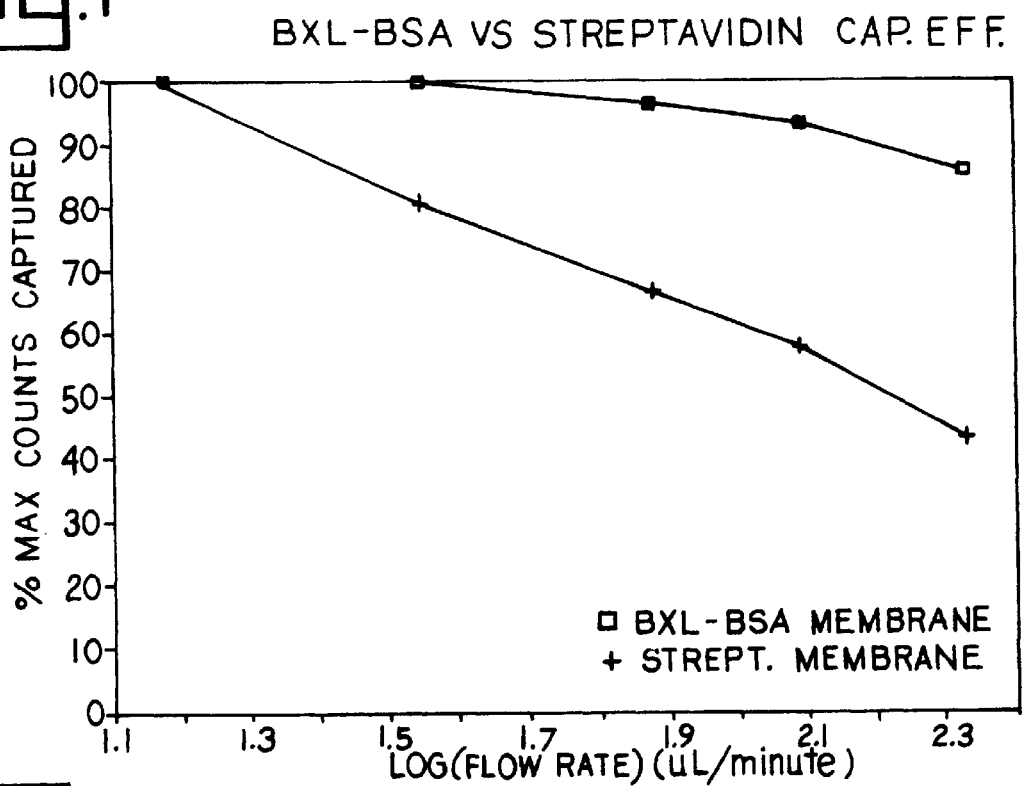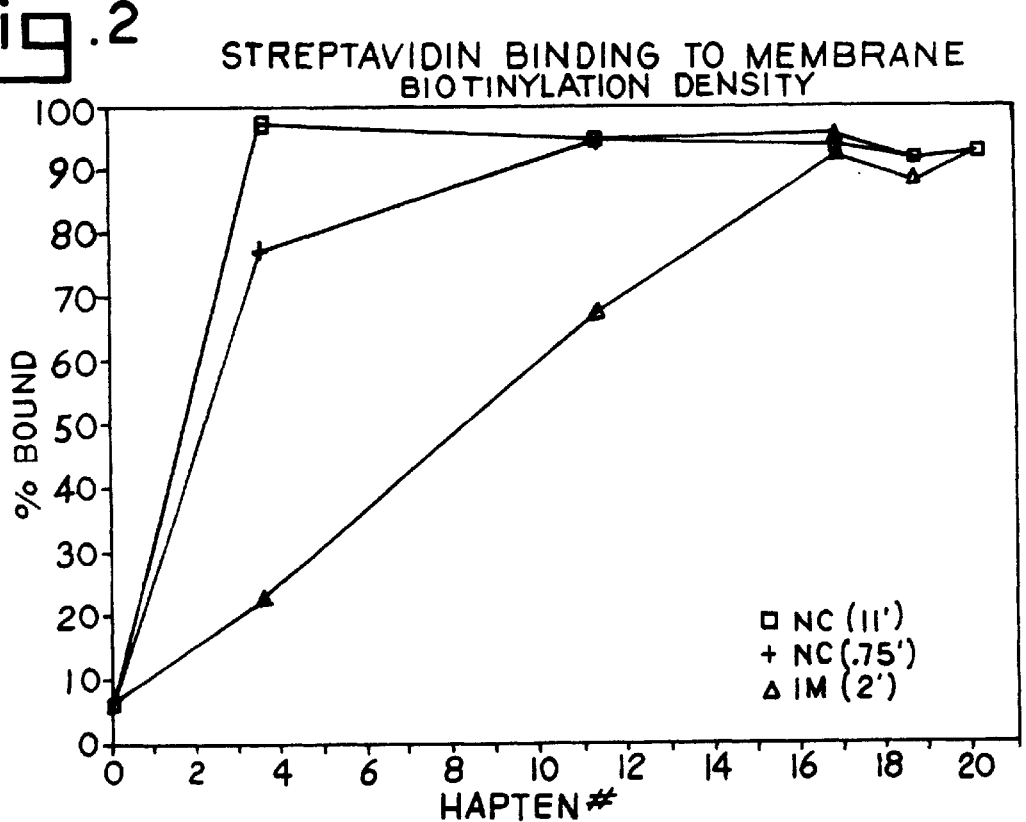

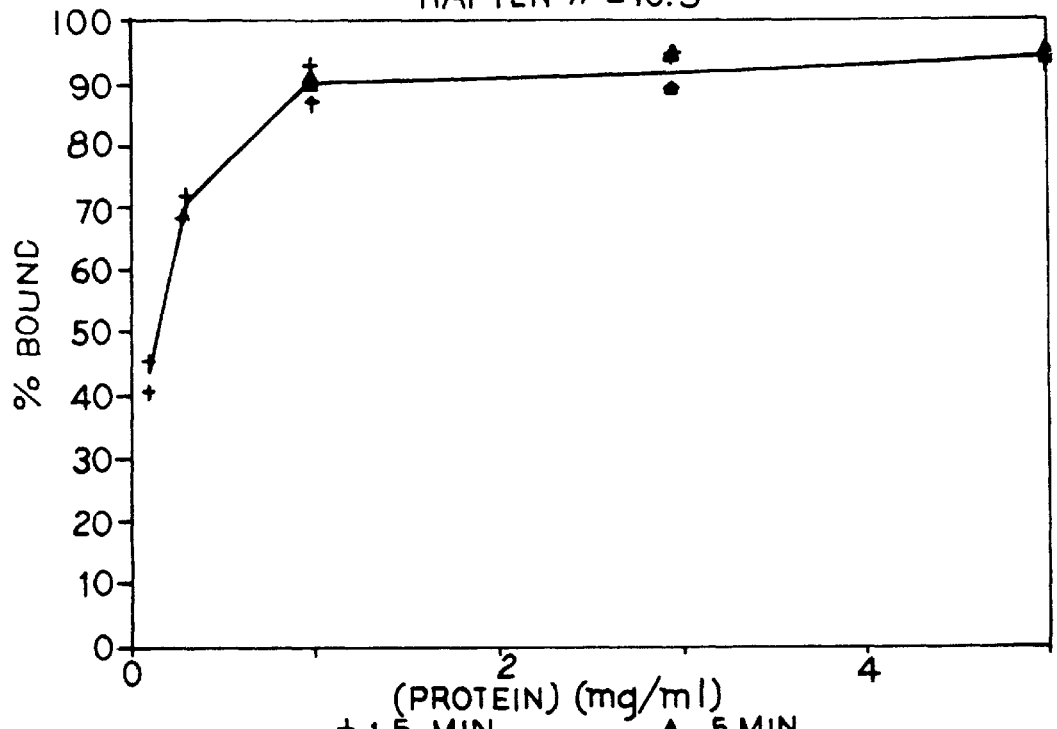
Fig. 3 CAPTURE EFFICIENCY OF 0.8 u NITROCELLULOSE HAPTEN # = 10.3
+ 1.5 MIN.   ▲ 5 MIN
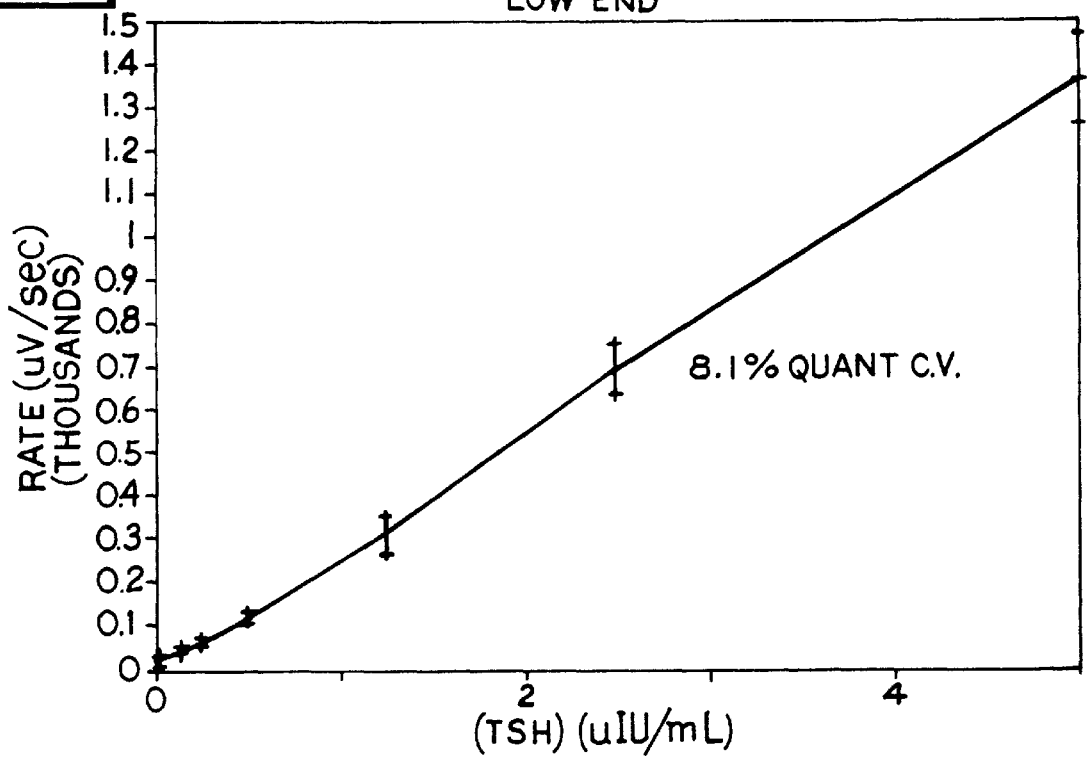
Fig. 4 TSH SENSOR ASSAY LOW END
8.1% QUANT C.V.

HAPTEN DERIVATIZED CAPTURE MEMBRANE AND DIAGNOSTIC ASSAYS USING SUCH MEMBRANE

This application is a continuation of U.S. application Ser. No. 08/364,522, filed Dec. 27, 1994, now abandoned which is a continuation of U.S. Ser. No. 07/490,644, filed May 24, 1990, now abandoned which is a continuation-in-part of U.S. Ser. No. 07/258,894, filed Oct. 17, 1988, now abandoned.

BACKGROUND OF THE INVENTION

1. Field of the Invention

This invention relates to a diagnostic reagents, capture membranes, which are useful in removing specifically binding complexes from solutions and assay methods using such reagents. The specifically binding complexes include antigen/antibody complexes, DNA, anti-DNA (antibody to DNA) or Single Strand DNA Binding Protein (such as SSB from *E. coli*), DNA, DNA hybrids, RNA, RNA hybrids, and similar specifically binding complexes.

2. The Related Art

There are extensive teachings in the art of diagnostic assays and reagents involving specifically binding complexes. Antigen/antibody reactions are widely used to determine antigen and antibodies. The labeling of members of these complexes with detectable markers such as enzymes or florescent dyes is well known. The binding of antigen or antibodies and solid supports as a means of removing complexes from solutions is also known. The use of haptens such as biotin and anti-haptens such as streptavidin in diagnostic assay is extensively discussed in a review article that appears in *Analytical Biochemistry* 171, 1–32 (1988).

Biotin attached to a solid-support is described in U.S. Pat. Nos. 4,282,287, 4,478,914, and 4,656,202. These patents describe precise layering technique wherein biotin is first attached to a solid-surface and the subsequent application of successive layers of avidin and extender results in a controlled modification of surface characteristics.

European Patent No. 87,307,850.5 is directed toward a method for routine plant-virus diagnosis which includes biotin attached to a macro-molecule that is conjugated to a sample of probe DNA. The probe containing compound is applied to a solid-matrix which has a test sample of DNA derived from plant tissue immobilized thereon. The presence of the target sequence is determined by washing the matrix with enzyme linked avidin followed by assaying for enzyme activity associated with the matrix.

U.S. Pat. No. 4,467,031 describes an enzyme-immunoassay which utilizes the biotin-avidin system as a convenient and stable linking group for connecting a reporter enzyme to an antibody.

U.S. Pat. No. 4,228,237 describes the use of the biotin-avidin system in a method for detection and determination of ligands. A surface having an antibody for the ligand of interest attached thereto is reacted with a sample of the ligand followed by a second ligand specific antibody that is conjugated with biotin. This complex is then reacted with an avidin conjugated enzyme and the results are determined by measurement of enzyme activity.

U.S. Pat. No. 4,656,025 describes a screening assay for tumor globulin. A tumor globulin-biotin conjugate on ELISA plates is reacted with avidin conjugated enzyme and quantification of the tumor globulin bound to the plate is determined by the application of the appropriate chromogenic substrate thereto.

U.S. Pat. No. 4,535,057 describes an immunoassay having biotin conjugated to a solid support through an antibody-virus complex. This biotin-antibody virus complex is then reacted with avidin conjugated to a reporter group or a label and the presence of the label associated with the surface is indicative of the presence of virus in the sample.

U.S. Pat. Nos. 4,727,019, and 4,632,901 describe an immunoassay wherein avidin is attached to a solid support and binds a ligand present in the sample to the support. U.S. Pat. No. 4,298,685 describes a diagnostic reagent that also involves avidin immobilized on a solid support. U.S. Pat. No. 4,582,810 describes a detection system wherein a suspension of particles having avidin covalently bound thereto reacts with a biotin-antibody complex to form a complex which results in a flocculent appearing solution.

U.S. Pat. No. 4,550,075 describes a method for ligand determination based on the biotin-avidin system without any solid support.

U.S. Pat. No. 4,486,530 describes an immunometric assay process that comprises a ternary complex of an antigenic substance, and a first and second antibody bound to the antigen in which the complex is removed from solution by filtering through a membrane.

Clinical Chemistry, 34, No. 8, p. 1585 (1988) describes a monoclonal antibody based noncompetitive avidin-biotin assay for luteinizing hormone (LH) in urine.

U.S. Pat. No. 4,778,751, describes a method for measuring antigens which comprises: forming in a liquid phase reaction a soluble complex wherein an antigen ($Ag_1$), antibody ($Ag_1$) or hapten (H) is linked through, respectively, a specific antibody (Ab), antigen (Ag) or anti-hapten (Anti-H), to a matrix which is soluble in the liquid phase and carries a ligand (X), the matrix capable of being chemically attached to more than one specific antibody (Ab), antigen (Ag) or anti-hapten (Anti-H); forming an insolubilized complex comprising a solid support linked to the ligand (X) of the soluble complex through an anti-ligand (Y), the insolubilized complex carrying a label (Z) linked to the antigen ($Ag_1$) through an anti-antigen (Anti-$Ag_1$), to the antibody ($Ab_1$) through an anti-antibody (Anti-$Ab_1$) or to the hapten (H); washing the insolubilized complex; and observing the washed insolubilized complex for the presence of the label (Z) wherein the presence of the label (Z) is an indication of the level of the antigen ($Ag_1$), antibody ($Ab_1$) or hapten (H) in the sample.

European Patent Application No. 86111379.3 describes multilayer immunoassay test devices involving the use of labeled reagents comprising a chemical group having a detectable physical property such as fluorescence or color.

European Patent Application No. 88.308164.8 describes a method for determination of single-stranded DNA based on the binding of a single-stranded DNA to a single-stranded DNA-binding protein to which is bound a solid support.

Molecular Immunology, 34: 221–230 (1989) describes an ELISA system involving immobilization of biotinylated CAbs through linkage by streptavidin to biotinylated carrier proteins absorbed on polystyrene. The present invention provides technology for removal of specifically binding complexes from a solution and differs from the prior art in that the reagent of this invention is a porous membrane with a hapten preferably biotin bound directly or indirectly to the membrane.

SUMMARY OF THE INVENTION

The present invention encompasses a capture membrane comprising a porous filter membrane having a hapten preferably biotin bound directly or indirectly to the membrane wherein specifically binding complexes having an antihapten preferably avidin or streptavidin bound to a binding member of the specifically binding complex are removed from a solution by the hapten when the solution flows through the membrane.

DETAILED DESCRIPTION OF THE INVENTION

As noted above, the present invention comprises a porous membrane or filter to which is bound a hapten; this membrane or filter being capable of filtering a solution that may contain a specifically binding complex having an anti-hapten bound to a binding member of the specifically binding complex.

The material of the membrane or filter is selected from material to which protein or other macromolecule can be adhered. A variety of materials may be used. Those skilled in the art will appreciate that porous membranes made of nylon, cellulose acetate, polyolefin, polyacrylamide, nitrocellulose or other porous materials may be employed in the present invention. Other synthetic or naturally occurring materials which will adhere a protein or other macromolecule may also be used. A preferred membrane is made from nitrocellulose.

Haptens are substances which do not elicit antibody formation unless complexed to macromolecules and which may be employed in the present invention as specific organic materials for which specific binding substances can be provided. Antibodies to haptens can be formed by binding the hapten to a protein to elicit an antibody response. A specific binding substance is any substance or group of substances having a specific binding affinity for the hapten to the exclusion of other substances. The employed hapten must be able to bind to a protein or other macro-molecule directly or through an extended linking group. Examples of haptens which may be used according to the instant invention include steroids such as estrone, estradiol, testosterone, pregnanediol and progesterone; vitamins such as $B_{12}$, biotin and folic acid; triiodothyronine, thyroxine, histamine, serotonin, digoxin, prostaglandins, adrenaline noradrenalin, morphine, vegetable hormones and antibiotics such as penicillin.

When the hapten is a substance having a naturally occurring receptor, the receptor can be utilized as the anti-hapten provided the receptor can be isolated in a form specific for the hapten. Illustrative haptens which have naturally occurring receptors include thyroxine, many steroids, polypeptides, such as insulin, angiotensin biotin and many others. Receptors for this class of haptens are usually proteins or nucleic acids.

Extended linking groups are groups that will bind the hapten to the protein or macro-molecule in such a way that the hapten has better access to the anti-hapten. Extended linking groups useful in the present invention include succinylated polylysine, dextran, polyethylene glycol, and preferentially a polyamido ether extending group. These extended linking groups may be used separately or in combination to obtain extended linking groups of varying lengths and binding properties. Extended linking groups are preferred for use with serum samples especially lipemic serum samples. Evidently, there are interfering substances in serum samples, the interference from which is overcome by the extended linking group. Where an extended linking group is not needed, a hapten such as biotin, without an extended binding group is bound to a functional group on a membrane or to a function group on a protein which can be disbursed on the membrane.

The extended linking group must be able to bind to the protein or macromolecule. Preferentially the extended linking group having an hapten bound to one end will be bound to the protein or macro-molecule with an amide bond; the amine of the amide bond arising from the protein and the carboxyl of the amide bond arising from the carboxy terminus of the extender group. Free carboxyl or hydroxyl groups on proteins can likewise be used.

The proteins and macro-molecule of the present invention include, but are not limited to, bovine serum albumin (BSA), bovine gamma globulin, and fibrinogen.

The complex produced by specific binding which is removed from the solution as it passes through the filter comprises two binding members and an antigen, with the proviso that one binding member is bound to an anti-hapten and the other binding member is bound co a labelling group.

The anti-haptens bound to the binding members of the present invention comprise the molecules described above that act as receptors to the above mentioned haptens. Antibodies are preferred binding members which are conveniently labeled with enzymes or fluorescent dyes and are also conveniently bound to anti-haptens such as avidin or antibodies to haptene.

This embodiment of the invention can be viewed as follows:

| Capture Membrane | Complex |
| --- | --- |
| membrane-hapten | anti hapten-Ab Ag Ab-(labeled) |
| membrane-(biotin) | (streptavidin)-Ab' Ag' Ab(enzyme) |

Persons having skill in the art will recognize that capture membranes may also be employed in sequential assays. In such an assay, a series of filtration steps is used to capture and detect a substance to be determined. Such an assay may have many advantages over standard, non-sequential assays.

For example, a solution of anti-hapten could be filtered through a haptenaced porous filter membrane, whereby the anti-hapten would be captured on the membrane. A solution containing an anti-hacpten binding substance would subsequently be filtered through the membrane, thereby capturing the anti-hapten binding substance. This anti-hapten binding substance may be a hapten or other substance which binds to an anti-hapten. The anti-hapten binding substance preferably is modified with binding sites for a substance to be determined. Filtering a solution of a substance to be determined through the membrane will capture the substance to be determined on the membrane. The substance to be determined may then be detected on the membrane by filtering and labeling the substance to be determined with a detectable label and detecting the label on the membrane. The label may then be detected by various methods in the art. For example, an electrode which is a semiconductor may be employed in one embodiment of the present invention.

Persons having skill in the art will recognize that many combinations of sequential assays may be performed. Complexes may be formed between anti-haptens, haptens, antigens, antibodies, substances to be determined and detectable labels. These complexes may have one or more components. Thus, assays may be designed to avoid interference from specific substances.

This embodiment of the invention can be viewed as follows:

| Capture Membrane | Complex |
| --- | --- |
| membrane-hapten antihapten | hapten-Ab Ag Ab-(labeled) |
| membrane-(biotin) (Streptavidin) | biotin-Ab' Ag' Ab-(enzyme) |

Antibodies may be determined in a manner similar to that for an antigen. Complexes may be formed between an anti-hapten, an antibody, an antigen bound to a hapten or anti-hapten and another antigen bound to a labeling group.

The haptens and anti-haptens comprise those molecules described above as haptens and anti-haptens. Antigens may be conveniently labeled with enzymes or fluorescent dyes and are also conveniently bound to haptens or anti-haptens.

These embodiments of the invention may be viewed as follows:

| Capture Membrane | Complex |
| --- | --- |
| membrane-hapten | anti-hapten hapten-Ag Ab Ag-labeled |
| membrane-(biotin) | (streptavidin)(biotin)-Ag Ab Ag-(enzyme) |

The antibodies employed in the present invention may be either polyclonal or monoclonal antibodies and are produced in response to the target antigen of the assay. Methods for the production of antibodies to various biological substances are well known in the art.

The antigens targeted by the assay include, but are not limited to antigens such as IgE, prostatic acid phosphatase, prostate specific antigen, alphafetoprotein, carcinoembryonic antigen, luteinizing hormone, creatine kinase MB, Human Chorionic Gonadotropin (HCG) and other antigens in serum, plasma, urine, or other liquid media.

Polydeoxyribonucleotides can be determined by reactions with single strand DNA binding protein (SSB) and anti-DNA antibodies. Thus, various combinations of labeled SSB or anti-DNA and biotinylated SSB or anti-DNA are employed. In this embodiment streptavidin is bound to the biotinylated SSB or anti-DNA so that the complex can be bound to the capture membrane having biotin. In place of SSB, an oligonucleotide probe may be used to detect DNA. The article in Biochemistry, 25:21 (1986) describes the large scale over production of single-strand binding protein (SSB) from *E. coli*. Monoclonal antibodies to DNA have been used to measure DNA in biological fluids, Journal of Immunological Methods, 88, (1986) 185–192.

These embodiments of the invention can be viewed as follows:

| Capture Membrane | Complex |
| --- | --- |
| membrane-biotin | streptavidin-biotin-anti-DNA/ DNA/SSB-enzyme |
| membrane-biotin | streptavidin-biotin-SSB/DNA/ anti-DNA-enzyme |
| membrane-biotin | streptavidin biotin-oligonucleotide probe/DNA/ oligonucleotide probe-enzyme |

Labeling groups that may be employed in the present invention include enzymes, fluorescent labels and radionuclides. The preferred label is an enzyme that is linked to the antibody at a position which does not interfere with the binding of the antibody to the antigen. Thus, the enzyme should possess potentially reactive groups to which the antibody can be coupled without destroying enzyme activity and should not occur naturally to an appreciable extent in the liquid Go be assayed for the specific biological substance. In addition, the enzyme should have a relatively long shelf life, a high specific activity and also be capable of being easily assayed, for example, with a visible light spectrophotometer.

Examples of enzymes which may conveniently be employed in the process of the present invention are, malate dehydrogenase, lipase, delta-5-ketosteroid isomerase, yeast alcohol dehydrogenase, yeast glucose-6-phosphate dehydrogenase, alpha glycerophosphate dehydrogenase, triose phosphate isomerase, horseradish peroxidase. alkaline phosphatase, asparaginase, glucose oxidase, beta-galactosidase, and more preferably, urease. Normally, it is preferred that the enzyme be in a pure form, free of contaminating proteins.

The preparation of the enzyme-labelled biological substances for use in the present invention can be accomplished in various ways known in the art. Examples of the coupling of biological substances to enzymes are described in, for example, L. A. Steinberger, Immunocytochemistry, Prentice Hall, New Jersey (1974).

Although a radionuclide such as $^{125}$I or $^{32}$P may also be used as the label non-radioactive labels are preferred.

After filtering the solution suspected of containing the antigen in a specifically binding complex through the porous filter membrane, the presence of labelled antibody on the porous membrane is then determined as an indication of the presence of the target antigen in the sample. In the case of an enzyme label this may be done by addition of a solution of a color forming substrate to the porous member to allow the substrate to react with the enzyme. Determinations can conveniently be made by the devices and methods described in U.S. Pat. Nos. 4,591,550, 4,704,353, and U.S. Pat. application Ser. No. 876,925, filed Jun. 20, 1986 and assigned to the same assignee as this application.

The invention is illustrated further by the following examples which are not to be construed as limiting the invention in scope or spirit to the specific procedures described in them.

BRIEF DESCRIPTION OF THE DRAWINGS

FIG. 1 illustrates the improved efficiency of the biotin membrane (BXL-BSA, biotinylated-Bovine Serum Albumin) versus the avidin (Streptavidin) membrane.

FIG. 2 illustrates the efficiency of capture of streptavidin at various densities of biotin using two different types of membrane and two different flow rates.

FIG. 3 illustrates the capture efficiency of 0.8$\mu$ nitrocellulose filter at various concentrations of BXL-BSA on the membrane and at various Streptavidin flow rates.

FIG. 4 illustrates the determination of TSH.

DESCRIPTION OF THE PREFERRED EMBODIMENTS

Figure 5:
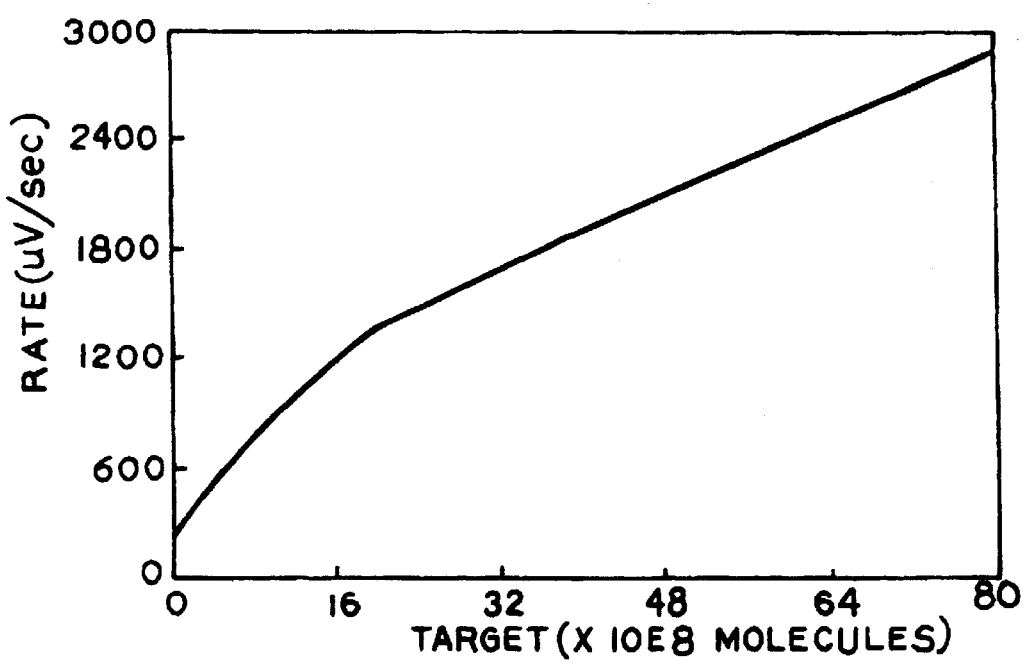
FIG. 5 is a standard curve generated by the dual probe assay.

A preferred capture membrane is made according to the following reaction scheme.

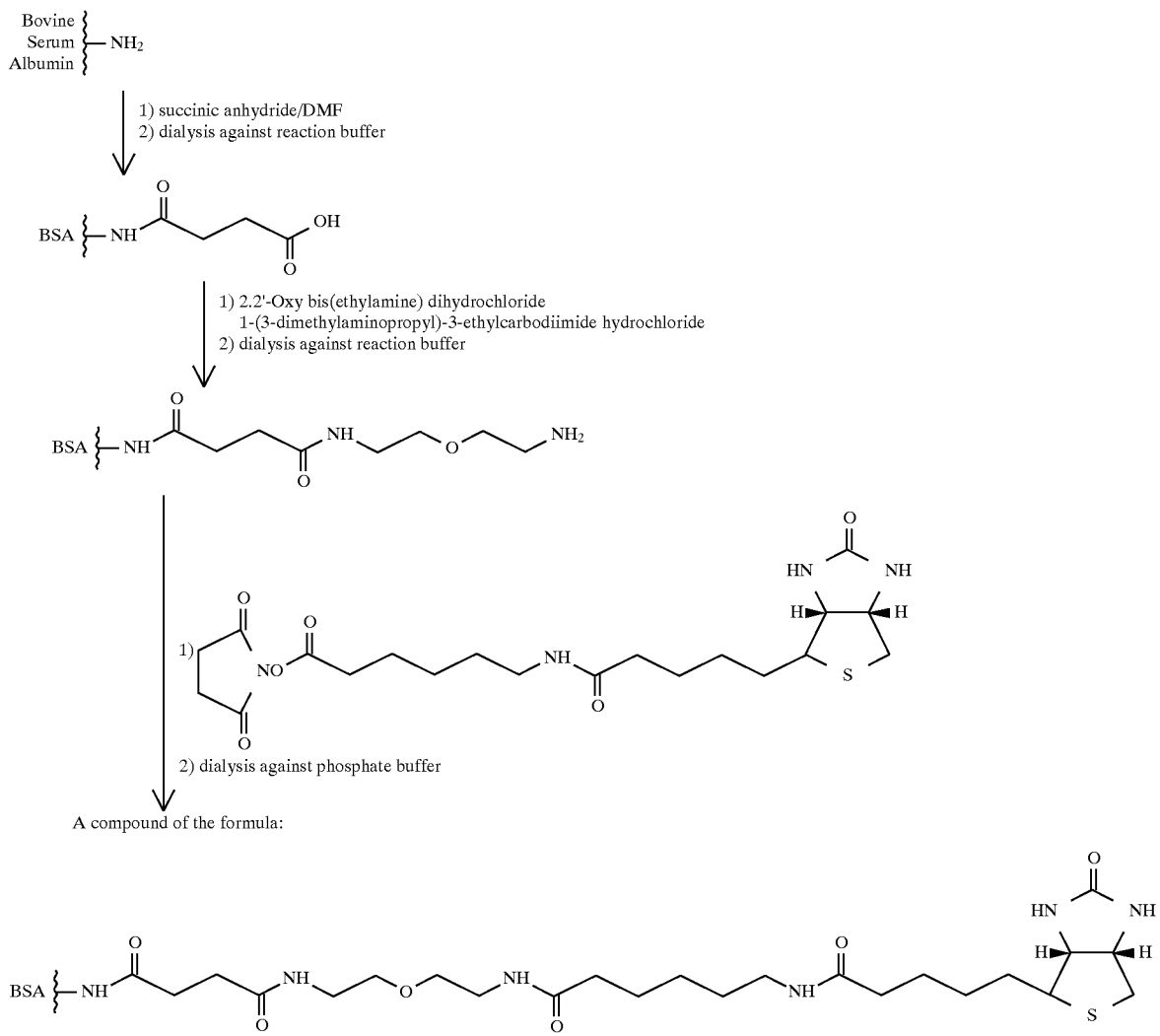

wherein 5–20 biotins with the extended linking group are bound to BSA.

Example 1

Preparation Of Capture Membrane

A pH 8.2 reaction buffer was prepared by dissolving 8.40 g sodium bicarbonate and 8.76 g sodium chloride in sufficient distilled water to make 1L of solution.

10.00 g Bovine Serum Albumin (BSA) was dissolved in 250 mL of pH 8.2 reaction buffer and the resulting BSA solution dialyzed exhaustively against reaction buffer with a dialysis filter. The volume after dialysis was still 250 mL.

The BSA concentration, as determined by absorbance at 280 nm at this point was 40 mg/mL. A TNBS assay performed on this BSA solution indicated 18 free amino groups per BSA. TNBS is a 2,4,6-trinitrobenzene sulfonic acid acid/sulfite based assay for free amino groups in a protein which is a modification of the procedure described by Palmer et al., *Clin. Chem.*, 15: 891–901, 1969. An aliquot was removed for later TNBS assays. To the BSA solution was then added 6.32 g of $K_2CO_3$ and the resulting solution was stirred vigorously as a solution of 3.34 g succinate anhydride in 83.5 mL DMF was added slowly over 14 minutes. The resulting solution was then stirred for an additional 5 minutes and allowed to stand at room temperature for one hour. The solution was then exhaustively dialyzed against reaction buffer and concentrated to 250 mL using a Minitan concentrator.

The BSA concentration at this point was determined by absorbance to be 40 mg/mL. A TNBS assay performed on the succinylated-BSA solution indicated less than one free amino group per succinylated-BSA.

At this point, 25 mL of a 1M solution of 2,2'-Oxy bis(ethylamine) dihydrochloride (pH 8.2) in reaction buffer was added to the stirred BSA solution. Next, 6.39 g of 1-(3-dimethylaminopropyl)-3-ethylcarbodiimide hydrochloride was added to the vigorously stirred BSA solution. Stirring was stopped after all of the carboduimide had dissolved and the resulting solution covered and incubated at room temperature for one hour.

The solution was then exhaustively dialyzed against reaction buffer and concentrated to 250 mL using a Minitan® (Millipore) concentrator.

The BSA concentration was again determined by absorbance to be 40 mg/mL. A TNBS assay run on the above prepared BSA-Oxy bis(ethylamine) solution indicated the presence of 15 free amino groups. A TNBS assay performed on the final dialysis buffer indicated sufficient dialysis of free amines from the BSA solution.

To the BSA solution was then added 1.51 g succinimidyl 6-(biotinamido) hexanoate and the solution was stirred vigorously for 5 minutes after which it was covered and incubated for one hour at room temperature.

The biotinylated-BSA solution was exhaustively dialyzed against a pH 7 phosphate buffer. The phosphate buffer was prepared as follows: 4.97 g of dibasic sodium phosphate, 2.07 g of monobasic sodium phosphate and 6.77 g of sodium chloride were dissolved in sufficient distilled water to make 1L of solution.

The concentration of biotinylated-BSA in solution after dialysis was determined by absorbance to be 15 mg/mL.

A TNBS assay performed on the biotinylated-BSA solution indicated the presence of three free amino groups. The difference between the three free amino groups on the biotinylated-BSA and 15 on the BSA-Oxy bis(ethylamine) is 12. This is the number of biotin molecules in the biotinylated-BSA.

$0.8\mu$ nitrocellulose membrane or Immobilon membrane was cut into sheets measuring 20 cm by 30 cm. 100 mL biotin immobilizing solution having 5 mg biotinylated BSA/mL phosphate buffer was placed in a trough.

The membrane is immersed into the protein solution. The wetted membrane was placed on the bottom of a glass dish, the dish inverted and the membrane incubated for 45 minutes. 500 mL of phosphate buffer was added to the dish and incubated for 15 minutes. This solution was then decanted.

A 0.1% glutaraldehyde fixing solution was prepared by adding sufficient phosphate buffer to 4 mL of a 25% glutaraldehyde solution to make 1L. 500 mL of this glutaraldehyde fixing solution was then added to the dish containing the nitrocellulose membrane, and the contents were incubated at room temperature for two hours. A solution of 0.1M ethanolamine pH 9.5 was added to a dish containing the Immobolin membrane and the contents were incubated at room temperature overnight.

After decanting the fixing solution or the ethanolamine, 500 mL phosphate buffer was added and the contents incubated for 15 minutes. The solution was again decanted, 500 mL distilled water added and the contents incubated for 15 minutes.

The water incubation was repeated once. The membrane was then inserted between two sheets of Whatman 3MM blotting paper to remove excess liquid and upon removal from the blotting paper was placed between fiberglass screen material. The screen holding the membrane was placed into a convection oven at 65° C. for 15 minutes.

The membrane was removed from the oven and placed into a vacuum desiccator at room temperature for storage.

Analysis of the Capture Efficiency of Membrane Coated with Biotin

The characteristics of binding at various flow rates of streptavidin to a biotin coated membrane (BXL-BSA) and of biotinylated BSA to a streptavidin coated membrane is shown in FIG. 1. Nitrocellulose membrane was coated with either streptavidin or BXL-BSA so as to allow the binding of approximately equivalent amounts of its corresponding binding partner. Three hundred uL of radiolabled streptavidin or BXL BSA was filtered through the appropriate membrane at various flow rates. The radioactivity captured on each membrane at the slowest flow rate was assigned 100% capture. The percentage of counts captured is plotted as a percentage of maximum capture against the log of the flow rate.

It is possible that the maximum flow rate tested was still too fast for the streptavidin membrane to capture 100% of the BXL-BSA since the capture curve had not begun to level off. However the biotin coated membrane was able to capture 95% of the streptavidin with a flow rate of 75 $\mu$L/minute whereas for the streptavidin membrane a flow rate of 17 $\mu$L/minute was needed to capture the same percentage of BXL-BSA.

The effect of biotin density (determined by the biotin/BSA ratio referred to as hapten number) on the capture of streptavidin is shown in FIG. 2. Two types of membranes were tested at various flow rates: 0.45 nitrocellulose [NC] and $0.65\mu$ Immobilon [IM] membrane. The latter, manufactured by Millipore Laboratories is a polyvinylidene difluoride based membrane which is coated with a hydrophilic polymer and is activated to allow covalent protein attachment. The membranes were coated with bovine serum albumin (BSA) which was labeled to various extent with biotin. The NC and IM membranes contained approximately 10 $\mu$g/cm$^2$ and 2 $\mu$g/cm$^2$ of BSA respectively. The numbers in parenthesis refer to the time taken for 300 $\mu$L of $^{125}$I-streptavidin to flow through the membrane. The figure shows that the higher the biotin density on the BSA the better the capture of streptavidin on the membrane. This is more evident on the IM membrane. The greater effect on the IM membrane is due to the lower amount of protein on the membrane. This can be concluded from the next figure (FIG. 3).

The effect of the protein loading on the ability of nitrocellulose membrane coated with biotin-BSA to capture streptavidin is shown in FIG. 3. Biotin-BSA, with a hapten number of 16.3, was immobilized onto nitrocellulose membrane at various concentrations. The X axis indicates the concentration of biotin-BSA employed to coat the membrane. The amount of biotin-BSA on the membrane is approximately 2.5, 5, 10, 30, 50 $\mu$g/cm$^2$. Three hundred $\mu$L or $^{125}$I-streptavidin was filtered through the membrane in 1.5 minutes and 5 minutes. The Y-axis represents the counts captured by the membrane as a percentage of the maximum counts bounds. As can be seen in the figure, the amount of biotin-BSA on the membrane also plays a role in the capture efficiency of streptavidin on the membranae.

The preceding figures demonstrate several key aspects of the invention: (1) Given equal binding capacities and at a given flow rate, the biotin coated membrane is more efficient at capturing streptavidin than the streptavidin coated membrane is at capturing biotin labeled protein. (2) Capture efficiency of the biotin membrane is determined by the biotin density on the membrane. The biotin density is controlled by both the hapten number on the BSA and by the amount of biotin-BSA on the membrane.

Use of Biotin Membrane in Assay for TSH

A pH 7.0 wash buffer was prepared to contain 100 mM sodium phosphate, 150 mM NaCl, 0.1% bovine gamma globulin and 0.05% of a surfactant such as polyoxyethylene sorbitan monooleate.

A nitrocellulose membrane was coated with biotinylated BSA (BXL-BSA) as described above. One square centimeter of the biotinylated membrane was mounted with transfer tape over a 6 mm diameter hole of a 1 cm×10 cm vinyl acetate stick.

The stick containing the membrane was placed into a filter unit, the upper portion of which is a funnel shaped cartridge having a 4 mm diameter opening that forces liquid to flow through the membrane.

A pH 7.4 conjugate-sample dilution buffer was prepared to contain 10 mM sodium phosphate, 150 mM NaCl, 10 mM Na$_2$SO$_3$, 1 mM 2-mercaptoethanol, 0.01% NaN$_3$, 0.1% bovine gamma globulin, 0.05% of a surfactant such as polyoxyethylene mono-oleate, 0.25% octoxynol, 1 mM EDTA. 2 µg/mL streptavidin-anti-thyroid stimulating hormone and 2 µg/mL urease-anti-thyroid stimulating hormone were added to the buffer solution immediately prior to running the assay. 750 µL conjugate-sample dilution buffer was added to 250 µL of serum and the resulting mixture incubated in a covered plastic tube for 1 hour at 37° C.

450 µL of this sample-conjugate mixture was filtered under vacuum via syringe pump through the mounted biotinylated membrane in three minutes.

The membrane was washed by filtering 500 µL of the pH 7.0 wash buffer through it in approximately 1 minute.

The stick was then removed from the filter unit and inserted into a sensor assembly having a silicon wafer. See the device of U.S. Pat. No. 4,591,550. The filtration area of the stick matched the light interrogated portion of the silicon wafer. Only one site of the reader was used and the plunger position was set at 70 µ from the silicon wafer surface. The reaction was monitored for 150 seconds for low signals (250 µV/sec) and for 50 seconds for higher signals. FIG. 4 illustrates the typical results for TSH determination.

Example 2

The Effect of Biotin Attachment Arm On The Recovery of Spiked TSH From Pooled Sera

| Capture Ligand Recovery | Sample | Rate | % |
|---|---|---|---|
| Biotin-BSA | Buffer | 1733 | "100" |
| Biotin-BSA | Sera | 191 | 11 |
| BXL-BSA | Buffer | 2592 | "100" |
| BXL-BSA | Sera | 2731 | 105 |

The table above indicates improvement in recovery of TSH from serum when the long chain form of biotin-BSA (BXL-BSA) is used compared with short-chain biotin-BSA (Biotin-BSA). The above results were obtained with the standard assay protocol described above. Either 1 mL pooled sera (sera) of conjugate-sample dilution buffer (buffer) was spiked with lng of TSH. Samples were normalized to the rates of the buffer samples (% recovery) for each type of membrane. In addition to the greater recovery in serum, the higher signal in buffer indicates a greater overall capture efficiency of the conjugate complex with BXL-BSA than with short chain biotin.

Example 3

DNA Assay Dose-Resnonse

Membrane: biotin-BSA coated nitrocellulose membrane (0.8 µ pore size).
DNA sample: 0, 5, 10, 25, 50 pg of single-stranded Calf thymus DNA in 200 µl of phosphate buffered saline (PBS).
Reagent: 1 µg/ml Streptavidin, 1 ng/ml SSB-urease, 10 ng/ml biotin-anti-DNA, 1% BSA in 10 mM Tris.HCl buffer, 1 mH EDTA (pH 7.4).
Assay Protocol: 200 µl of DNA sample was incubated with 500 µl of reagent at 37° for 30 minutes. The mixture was filtered through the biotin-BSA coated membrane at a flow rate of about 100 µl/min. The membrane was then washed with 1 cc of pH 5 wash buffer (1 mM sodium acetate, 0.1M NaCl, 0.05% polyoxyethylene mono-oleate) at a maximuim flow rate of about 6 ml/min). After washing, the membrane was transferred to pH sensor chambers (U.S. Pat. No. 4,591,550), containing the substrate (pH 5 wash plus 100 mM urea) and the pH response was read.

Results

| DNA (Pg/sample) | (µV/sec) Rate of Signal |
|---|---|
| 0 | 62 ± 3 |
| 5 | 106 ± 7 |
| 10 | 156 ± 10 |
| 25 | 310 ± 1 |
| 50 | 778 ± 70 |

Example 4

Detection Of DNA In Insulin And Granulocyte Macrophage Colony Stimulating Factor (CMCSF) SaMiles Membrane: biotin-bSA coated nitrocellulose membrane (0.8µ pore size).
Pre-treatment of Porcine Insulin: 10 mg/mL insulin (in 10 mM tris buffer, 1 mM EDTA, pH 8.5) was digested with 100 µg/mL of proteinase K at 55°, overnight. 0, 5, and 50 pg of calf thymus DNA were spiked into 1 mg of insulin digest. In another set of experiments, 0, 5, and 50pg of calf-thymus DNA were spiked into PBS solution containing 0.4 mg of GMCSF (total volume was 200 µl). All samples were heated at 100° C. for 5 minutes to inactivate proteinase K and denature DNA to single-stranded. Insulin samples were cooled on ice and GMCSF samples were cooled down to room temperature.

200 µl of sample was mixed with 500 µl of reagent (200 ng/ml streptavidin, 2.5 ng/ml biotin-SSB, 9 ng/ml urease-anti-DNA; in 1% BSA, 0.25% octoxynol, 10 mM Tris.HCl buffer, 1 mM EDTA, pH 7.5).

The samples were incubated at 37° for 30 minutes and filtered through the membrane. 1 cc of wash solution 5 mM sodium phosphate, pH 7, 0.1 M NaCl 0.05% polyoxyethylene sorbitan mono-oleate) was filtered through the membrane twice. The signal was read with a pH sensor of the type described in U.S. Pat. No. 4,591,550.

Results

| Sample | Rate (µV/sec) |
|---|---|
| insulin | 39 |
| insulin + 5 pg DNA | 56 |
| insulin + 50 pg DNA | 254 |
| GMCSF | 21 |
| GMCSF + 5 pg DNA | 40 |
| GMCSF + 50 pg DNA | 192 |

Example 5

Dual Probe Assay

Dual probe assay mixtures were prepared to contain 1:2 serial dilutions of Hinfl digested pGEM3 starting at 25 ng (7.8×10$^9$ target molecules) per assay mixture, 2 ng of 5' biotinylated 20 mer (CCAGTTACCTTCGGAAAAAG), and 0.5 ng of 5' fluoresceinated 20 mer (TAGCTCTTGATCCGGCAAAC) in 100 µl of 3× PBSE (a pH 7.4 solution containing 30 mM sodium phosphate, 450 mM NaCl, and 3 mM EDTA) having 0.25% of a surfactant such as polyoxyethylene sorbitan mono-oleate. This sequence of each 20-mer is also found on the same HinfI fragment of pGEM3. The sample DNA was then denatured by heating the mixture to 100° C. for 5 minutes.

The mixture was subsequently incubated at 50°to 55° C. for 30 minutes. To the mixture was then added 1 ml of a solution prepared to contain 1 µg/ml streptavidin, 8 µg/ml anti-fluorescein-urease conjugate in 3× PBSE, 0.25% polyoxyethylene sorbitan mono-oleate, 1 mg/ml BSA and 80 µM N-acetylcysteine. This resulting conjugate solution was incubated for 30 minutes at room temperature.

The incubated conjugate solution was then filtered through a biotin coated nitrocellulose membrane mounted on a plastic stick. Next, 1 ml of threshold wash (10 mM sodium phosphate, 100 mM NaCl, 0.05% polyoxyethylene sorbitan mono-oleate, and 0.05% NaN$_3$, pH 6.5) was filtered through the membrane after the conjugate solution and the membrane was dipped into 50 ml of threshold wash. The stick was then inserted into a pH sensor chamber of the type described in U.S. Pat. No. 4,591,550 containing substrate solution (100 mM urea in threshold wash). The pH response was then read yielding the results displayed in FIG. 5.

Example 6

Application of Dual Probe Assay to Polyerase Chain Reaction (PCR)

1. Amplification of 0.1 kbp region in pGEM3 using PCR

A polymerase chain reaction (PCR) mixture was prepared to contain 100 mM Tris.HCl (pH 8.3), 10 mM MgCl3, 1 mM each dNTP, 1 µM primer 1(CAAAAAAACCACCGGTACCAG), 1 µM primer 2 (AGTATTTGGTATCTGCGCTCTG), 10 pg pGEM3 (3.15× $10^6$ target molecules) previously digested with HifI. The region to be amplified contains each of the 20-mer sequences described in Example 5. This PCR mixture was incubated at 100° C. for 5 minutes.

Immediately after incubation, 2 µl of 5U/µl Taq Polymerase (Perkin Elmer) was added to the PCR mixture which was thoroughly mixed and then incubated at 94° C.

Using an Eppendorf thermal cycler, the incubation temperature was cycled between 94° C. and 55° C. The thermal cycler was set so that each cycle lasted about 3 minutes. PCR samples were removed from the mixture in the cycler at cycles 13, 15 and 17 when the temperature reached 56° C. These samples were stored at −20° C. for later use in the dual probe assay. Blank samples which did not contain pGEM3 DNA were prepared similarly for use as a negative control.

2. Dual Probe Assay using PCR Sample

10 µl of a PCR sample prepared above was combined with 90 µl of the dual probe assay mixture prepared in Example 5 and the entire 100 µl mixture was denatured at 100° C. for 5 minutes.

The mixture was subsequently incubated at 50° to 55° C. for 30 minutes. To the mixture was then added 1 ml of a solution prepared to contain 1 µg/ml streptavidin, 8 µg/ml antifluorescein-urease conjugate in 3× PBSE, 0,25% polyoxyethylene sorbitan mono-oleate, 1 mg/ml BSA and 80 µM N-acetylcysteine. This resulting conjugate solution was incubated for 30 minutes at room temperature.

The incubated conjugate solution was then filtered through a biotin coated nitrocellulose membrane mounted on a plastic stick. Next, 1 ml of threshold wash (10 mM sodium phosphate, 100 mH NaCl, 0.05% polyoxyethylene sorbitan mono-oleate, and 0.05% NaN$_3$, pH 6.5) was filtered through the membrane after the conjugate solution. The stick mounted membrane was dipped into 50 ml of threshold wash and then inserted into a pH sensor chamber of the type described in U.S. Pat. No. 4,591,550 containing substrate solution (100 mM urea in threshold wash). The pH response was then read yielding the results displayed in FIGS. 6 and 7.

Figure 6:
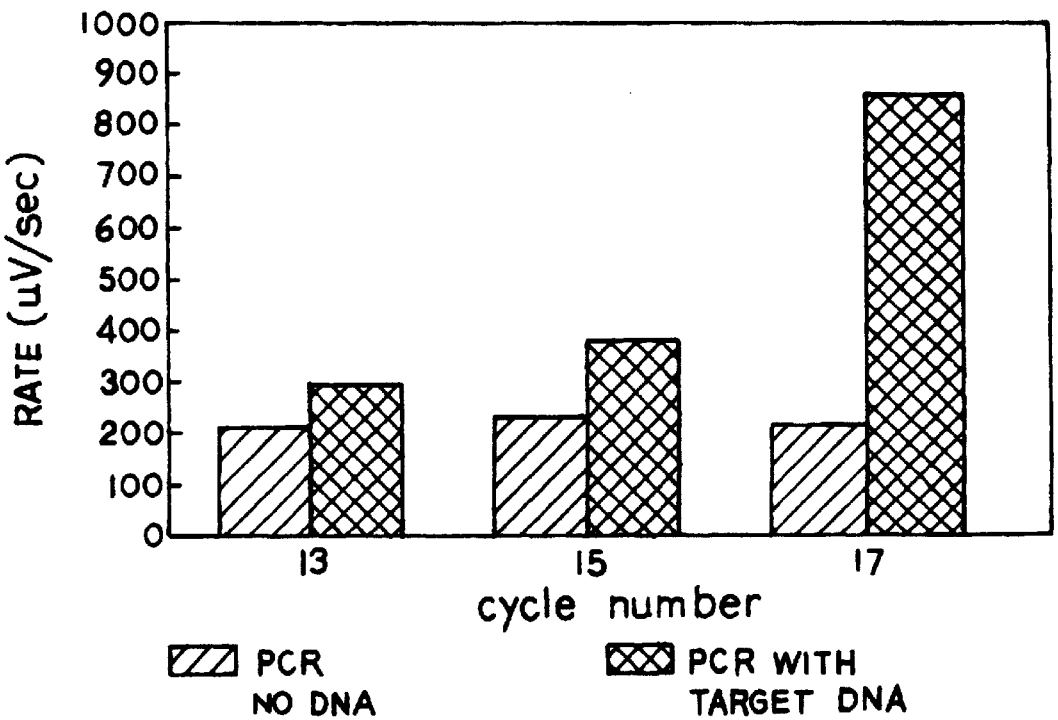
FIG. 6 is a semilog plot illustrating amounts of polymerase chain reaction (PCR) product determined by the dual probe assay.
Figure 7:
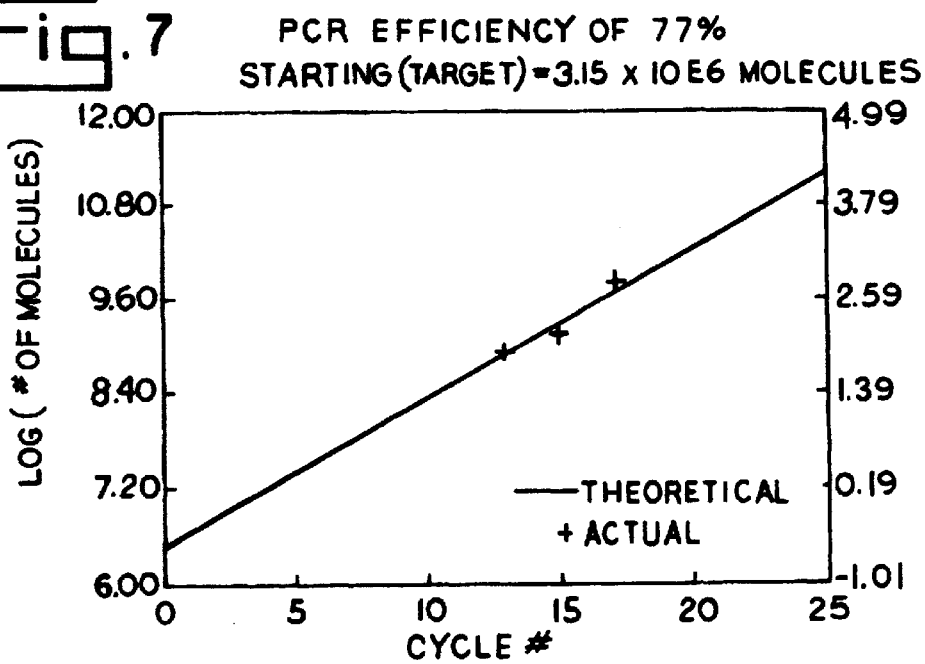
FIG. 7 is a graph of the efficiency of the PCR determined using the dual probe assay.

The specific signal (the difference between the signals from the samples with and without target DNA) increases more than linearly from cycle 13 to cycle 17 (FIG. 6). FIG. 3 shows the amount of specific signal from cycles 13, 15, and 17 on a semilog plot. This graph suggests that the amount of specific signal and therefore PCR product, as determined by comparison with the amount of specific signal generated by known amounts of plasmid DNA (e.g., FIG. 5), increases exponentially from cycle 13 to cycle 17. The increase in specific signal per cycle fits a line that implies that the PCR amplification factor is 1.54 per cycle. Since the theoretical PCR factor is 2.00, the apparent efficiency is 77%.

The kind of measurements taken in this experiment have at least two potential uses. First, the determination of amplification factor is useful in experimental optimization of PCR conditions. For example, there is clearly room for further optimization in the experiment described above. Second, the exponential plot shown in FIG. 7 can be used to determine by extrapolation the amount of starting analyte. For example, the amount of nucleic acid from a pathogen, such as HIV, could be determined. This would be useful in assessing the response to a therapeutic regimen.

Example 7

A. Simultaneous and Sequential Determination of Murine IgG

1. Simultaneous Determination Procedure

A mixture was prepared to contain MuIgG, biotinylated-anti-MuIgG, fluoresceinated-anti-MuIgG, streptavidin, and anti-fluorescein-urease. This resulting mixture was incubated for 1 hour at 37° C.

Figure 8:
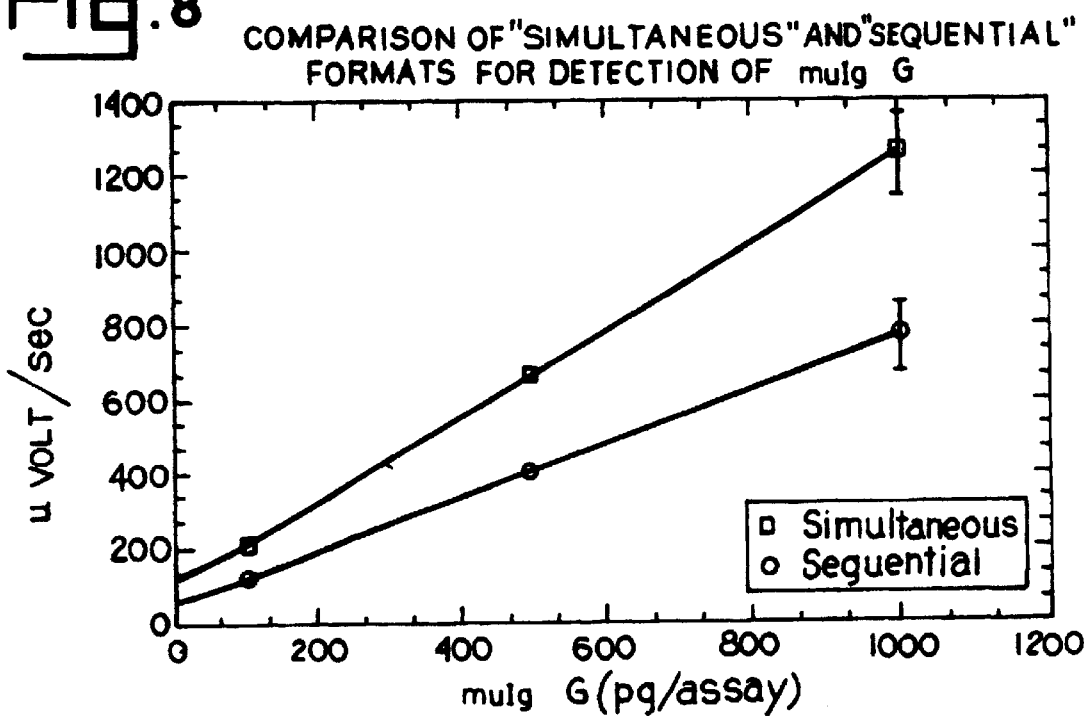
FIG. 8 is standard curves for the determination of MuIgG by sequential and simultaneous procedures.

Assay buffer was added to the incubated mixture which was then filtered over a period of 15 minutes through a biotin coated nitrocellulose membrane mounted on a plastic stick. The membrane was washed with pH 7.0 phosphate wash buffer over 5 minutes. The stick as then inserted into a pH sensor chamber of the type described in U.S. Pat. No. 4,591,550 containing substrate solution (urea in threshold wash). The pH response was then read yielding the results shown in the following table and FIG. 8.

2. Sequential Determination Procedure

A mixture of MuIgG, biotinylated-anti-MuIgG and fluoresceinated-anti-MuIgG was prepared and incubated for 1 hour at 37° C. To this incubated mixture was then added streptavidin. The resulting mixture containing streptavidin was filtered over a period of 10 minutes through a biotin coated nitrocellulose membrane mounted on a plastic stick. The membrane was then washed with pH 7.0 phosphate wash buffer over 5 minutes.

A solution of anti-fluorescein-urease was next filtered over 5 minutes through the membrane which was subsequently washed over 5 minutes with pH 7.0 phosphate wash buffer. The stick was then inserted into a pH sensor chamber of the type described in U.S. Pat. No. 4,591,550 containing substrate solution (urea in threshold wash). The pH response was then read yielding the results shown in the following table and FIG. 8.

Determination of Shrine IgG by Simultaneous and Sequential Procedures

| | Sequential | |
|---|---|---|
| pg MuIgG | μvolt/sec | S.D. (n = 4) |
| 0 | 54 | 3.0 |
| 100 | 124 | 3.0 |
| 500 | 403 | 16 |
| 1000 | 758 | 93 |

| | Simultaneous | |
|---|---|---|
| pg MuIgG | μvolt/sec | S.D. (n- = 4) |
| 0 | 120 | 11 |
| 100 | 209 | 11 |
| 500 | 658 | 24 |
| 1000 | 1247 | 112 |

Example 8

Simultaneous and Sequential Determinations of Anti-Human Chorionic Gonadotropin Human chorionic gonadotropin (HCG) was labeled with biotin to yield biotinylated HCG. Another sample of HCG was labeled with fluorescein to yield fluoresceinated HCG.

1. Sequential Determination of Anti-HCG

400 μl samples were prepared to contain 0, 4, 20 and 100 ng of anti-HCG. Each sample was combined with 100 μl of solution containing 10 ng of biotinylated HCG and 10 ng of fluoresceinated HCG and the resulting 500 μl mixtures were incubated for 1 hour at room temperature.

To each incubated mixture was then added 500 μl of a 4 ng/ml streptavidin solution and after mixing, were filtered through a biotin coated nitrocellulose membrane mounted on a plastic stick. Each membrane was then washed with 2 ml of pH 7.0 phosphate wash buffer. 500 μl of a 4 pg/ml solution of urease-anti-fluorescein was filtered through the membrane which was again washed with 2 ml of the phosphate wash buffer.

The sticks were then inserted into a pH sensor chamber of the type described in U.S. Pat. No. 4,591,550 containing urease substrate solution. The pH response was read generating the results displayed in the table below.

2. Simultaneous Determination of Anti-HCG

100 μl samples were prepared to contain 0, 4, 20, and 100 μl of anti-HCG. Each sample was mixed with 100 μl of the biotinylated-HCG, fluoresceinated HCG solution used in part 1 of this example and with 100 μl of the 4 μg/m urease-anti-fluorescein solution. The resulting mixture was incubated for 1 hour and 20 minutes at room temperature. To each table was added 1 ml of assay buffer and the resulting mixture filtered through a biotin coated nitrocellulose membrane mounted on a plastic stick. The membrane was washed with 2 ml of wash buffer and read in a pH sensor as described above. The results are displayed below.

This sequential antibody assay may be used to measure an immune antibody response to a vaccine. The specific antibody may be detected at concentrations as low as 1%.

Sequential and Simultaneous Determination of anti-HCG

| | Rate (μv/sec) | |
|---|---|---|
| Anti-HCG (ng) | Sequential | Simultaneous |
| 0 | 115 ± 4 | 120 ± 15 |
| 4 | 130 ± 6 | 121 ± 2 |
| 20 | 187 ± 7 | 165 ± 7 |
| 100 | 500 ± 20 | 271 ± 17 |

Example 9

DNA Dose Response Assay-Alternate Configuration

DNA samples were prepared to contain OP 5, 10, 25, 50, 100, 150 and 200 pg of single-stranded DNA in 500 μL of phosphate buffered saline. A dose-response reagent was prepared to contain 5 pg/mL streptavidin, 2.25 ng/mL biotinylated single-stranded binding protein, and 93.8 ng/mL anti-DNA urease in Tris-EDTA formulation buffer. The 500 μL DNA samples were heat-denatured at 95° C. for 10 minutes and subsequently cooled and combined with 1.0 mL of dose-response reagent. These mixtures were incubated at 37° C. for 1 hour and each was filtered through a biotin-BSA coated nitro-cellulose membrane mounted on a plastic stick. Each membrane was washed with pH 6.5, 10 mm phosphate buffer and the stick inserted into a pH sensor chamber of the type described in U.S. Pat. No. 4,591,550 containing urease-substrate. The pH response was read generating the data in the table below.

| | Results | | |
|---|---|---|---|
| pg DNA | Rate (μvolt/sec, mean of 8 tests) | Standard Deviation | Coefficient of Variance (%) |
| 0 | 76.3 | 12.7 | 16.0 |
| 5 | 148 | 15.6 | 13.5 |
| 10 | 222 | 35.2 | 15.9 |
| 25 | 488 | 23.3 | 4.6 |
| 50 | 981 | 50.9 | 5.2 |
| 100 | 2048 | 61.3 | 3.0 |
| 150 | 3145 | 112.6 | 3.5 |
| 200 | 4662 | 189.5 | 4.1 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for determining single or double stranded DNA in a mixture suspected of containing said DNA, comprising:
    (a) preparing a solution of first and second binding members and a portion of the mixture suspected to contain said DNA,
        the first binding member being anti-DNA, single-stranded binding protein, or an oligonucleotide probe complimentary to at least a portion of the DNA directly or indirectly bound to avidin or streptavidin,
        the second binding member being anti-DNA, single-stranded binding protein, or an oligonucleotide probe complimentary to at least a portion of the DNA directly or indirectly bound to a detectable label, where the binding members in the presence of DNA in the mixture form a specifically binding complex between the DNA and the binding members;

(b) filtering the solution through a filter membrane having adhered thereto a compound of the formula:

$$\left[ \text{protein} - \text{NH} - \overset{O}{\underset{}{C}} - \text{CH}_2\text{CH}_2 - \overset{O}{\underset{}{C}} - \overset{H}{N} - \text{CH}_2\text{CH}_2 - O - \text{CH}_2\text{CH}_2 - \overset{H}{N} - \right.$$

$$\left. \overset{O}{\underset{}{C}} - (\text{CH}_2)_4 - \overset{H}{N} - \overset{O}{\underset{}{C}} - (\text{CH}_2)_3 - \text{CH} - \text{CH} - \overset{H}{\underset{S}{\bigtriangleup}} - \text{CH}_2 - \overset{H}{\text{CH}} \cdots \text{NH} - \overset{O}{\underset{}{C}} \cdots \right]_n$$

where n is an integer of at least 5; and (c) detecting the label.

2. A method for determining single or double stranded DNA in a mixture suspected of containing said DNA, comprising:

(a) preparing a solution of a binding member linked to avidin or streptavidin, the binding member having a binding affinity for the DNA to be determined; and (b) filtering the solution through a filter membrane having adhered thereto a compound of the formula:

$$\left[ \text{protein} - \text{NH} - \overset{O}{\underset{}{C}} - \text{CH}_2\text{CH}_2 - \overset{O}{\underset{}{C}} - \overset{H}{N} - \text{CH}_2\text{CH}_2 - O - \text{CH}_2\text{CH}_2 - \overset{H}{N} - \right.$$

$$\left. \overset{O}{\underset{}{C}} - (\text{CH}_2)_4 - \overset{H}{N} - \overset{O}{\underset{}{C}} - (\text{CH}_2)_3 - \text{CH} - \text{CH} - \overset{H}{\underset{S}{\bigtriangleup}} - \text{CH}_2 - \overset{H}{\text{CH}} \cdots \text{NH} - \overset{O}{\underset{}{C}} \cdots \right]_n$$

where n is an integer of at least 5.

3. A method according to claim 1, wherein n is an integer of from 5 to about 20.

4. A method according to claim 1, wherein the protein is Bovine Serum Albumin.

5. A method according to claim 4, wherein n is from 5–20.

6. A methods according to claim 3, wherein the protein is Bovine Serum Albumin.

7. A method according to claim 1, wherein the binding members are antibodies.

8. A method according to claim 1, wherein the membrane comprises nitrocelluloses.

9. A method according to claim 1, wherein the label is an enzyme.

10. A method according to claim 1, wherein the label is detected by an electrode.

11. A method according to claim 10, wherein the electrode is a semiconductor.

12. A method according to claim 2, further comprising (c) filtering a solution suspected to contain the substance to be determined through the membrane.

13. A method according to claim 12, further comprising (d) filtering a solution of a detectable label linked to a binding member, the binding member having a binding affinity for the substance to be determined.

14. A method according to claim 13, further comprising detecting the label .

15. A method according to claim 2, wherein the protein is Bovine Serum Albumin.

16. A method according to claim 15, wherein n is from 5–20.

17. A method according to claim 2, further comprising (c) filtering a second solution through the membrane, the second solution containing a detectable label linked to a binding member, the binding member having a binding affinity for the substance to be determined, and the second solution being suspected to contain the substance to be determined.

18. A membrane according to claim 17, wherein the porous membrane comprises nitrocellulose.

19. A method according to claim 13, wherein the porous membrane comprises nitrocellulose.

20. A method according to claim 1, wherein the first binding memberis biotin-anti-DNA.

21. A method according to claim 1, wherein the second binding member is labeled single stranded binding protein.

22. A method according to claim 1, wherein the second binding member is labeled anti-DNA.

23. A method according to claim 1, wherein the first binding member is biotin-single stranded binding protein.

24. A method according to claim 2, wherein the first binding member is biotin-anti-DNA.

25. A method according to claim 2, wherein the second binding member is labeled single stranded binding protein.

26. A method according to claim 2, wherein the second binding member is labeled anti-DNA.

27. A method according to claim 2, wherein the first binding member is biotin-single stranded binding protein.

* * * * *